United States Patent [19]

Strike

[11] 3,933,904

[45] Jan. 20, 1976

[54] 11,15-DIHYDROXY-9,13-PROSTADIENOIC ACID

[75] Inventor: Donald P. Strike, Saint Davids, Pa.

[73] Assignee: American Home Products Corporation, New York, N.Y.

[22] Filed: Sept. 13, 1974

[21] Appl. No.: 505,804

[52] U.S. Cl...... 260/514 D; 260/348 A; 260/468 D; 934/305; 934/317
[51] Int. Cl.$^2$.................. C07C 61/38; C07c 69/74
[58] Field of Search.................. 260/468 D, 514 D

[56] References Cited
UNITED STATES PATENTS 3,862,979  1/1975  Gandolfi et al. .................. 260/514

*Primary Examiner*—Robert Gerstl
*Attorney, Agent, or Firm*—Robert Wiser

[57] ABSTRACT

Derivatives are prepared from 10,11α-epoxy-PGA$_2$. The derivatives are new compounds, such as 9,10-dehydro-9-deoxy-PGF$_2$, not heretofore found in nature which possess various pharmacological activities, one of which is bronchodilation.

2 Claims, 1 Drawing Figure

11,15-DIHYDROXY-9,13-PROSTADIENOIC ACID

BACKGROUND OF THE INVENTION

The prostaglandins are a group of hormone-like substances which may be viewed as derivatives of prostanoic acid. Several prostaglandins are found widely distributed in mammalian tissue and have been isolated from this source. These prostaglandins have been shown to possess a variety of biological properties such as bronchodilation and the ability to reduce gastric secretion.

The present invention concerns $PGF_1$ and $PGF_2$ derivatives in which the 9 and 10-positions, (using the prostanoic acid numbering system) have together lost the elements of water with addition of a new 9,10-carbon to carbon bond, i.e. the 9,10-positions of $PGF_1$ and $PGF_2$ have suffered the equivalent of a selective dehydration. The preparation of the starting material for this series, $10,11\alpha$-epoxy-$PGA_2$, is reported in J. Org. Chem. 38, 3187 (1973).

Summary of the Invention

The invention sought to be patented in a first composition aspect resides in the concept of a chemical compound of the structure

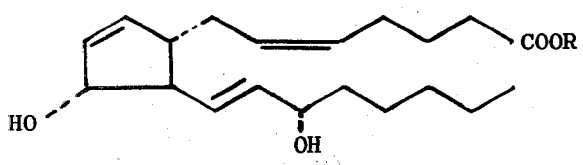

wherein R is hydrogen or alkyl of from 1 to 6 carbon atoms.

The tangible embodiments of the first composition aspect of the invention possess the inherent general physical properties of being clear to yellow oils, are substantially insoluble in water and are generally soluble in organic solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, and the mode of synthesis, confirm the structures of the compositions sought to be patented.

The tangible embodiments of the first composition aspect of the invention possess the inherent applied use characteristic of exerting gastric anti-secretory and bronchodilating effects, upon administration to warm-blooded animals. In addition, they inhibit blood platelet adhesiveness, in vitro, which indicates their usefulness as blood platelet anti-aggregation agents. These effects are evidenced by pharmacological evaluation according to standard test procedures.

The invention sought to be patented in a second composition aspect resides in the concept of a chemical compound of the structure

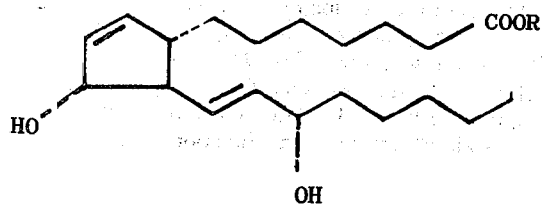

wherein R is H or alkyl of from 1 to 6 carbon atoms.

The tangible embodiments of the second composition aspect of the invention possess the inherent general physical properties of being either crystalline solids or clear to yellow oils, are substantially insoluble in water and are generally soluble in polar solvents such as ethyl acetate and ether. Examination of compounds produced according to the hereinafter described process reveals, upon infra-red, nuclear magnetic resonance, and mass spectrographic analysis, spectral data supporting the molecular structures herein set forth. The aforementioned physical characteristics, taken together with the nature of the starting materials, and the mode of synthesis, confirm the structure of the compositions sought to be patented.

The tangible embodiments of the second composition aspect of the invention possess the inherent applied use characteristic of exerting hypotensive, gastric anti-secretory, and bronchodilating effects upon administration to warm-blooded animals. In addition, they inhibit blood platelet adhesiveness, in vitro, which indicates their usefulness as blood platelet anti-aggregation agents. These effects are evidenced by pharmacological evaluation according to standard test procedures.

The invention sought to be patented in a third composition aspect resides in the concept of a chemical compound of the structure

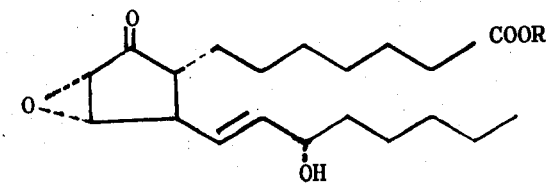

wherein R is hydrogen or alkyl of from 1 to 6 carbon atoms.

The tangible embodiments of the third composition aspect of the invention possess the inherent general physical properties of being clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, and the mode of synthesis, confirm the structure of the compositions sought to be patented.

The tangible embodiments of the third composition aspect of the invention possess the inherent applied use characteristic of being intermediates in the synthesis of the embodiments of the second composition aspect of the invention.

DESCRIPTION OF THE PREFERRED EMBODIMENTS

Figure 1:
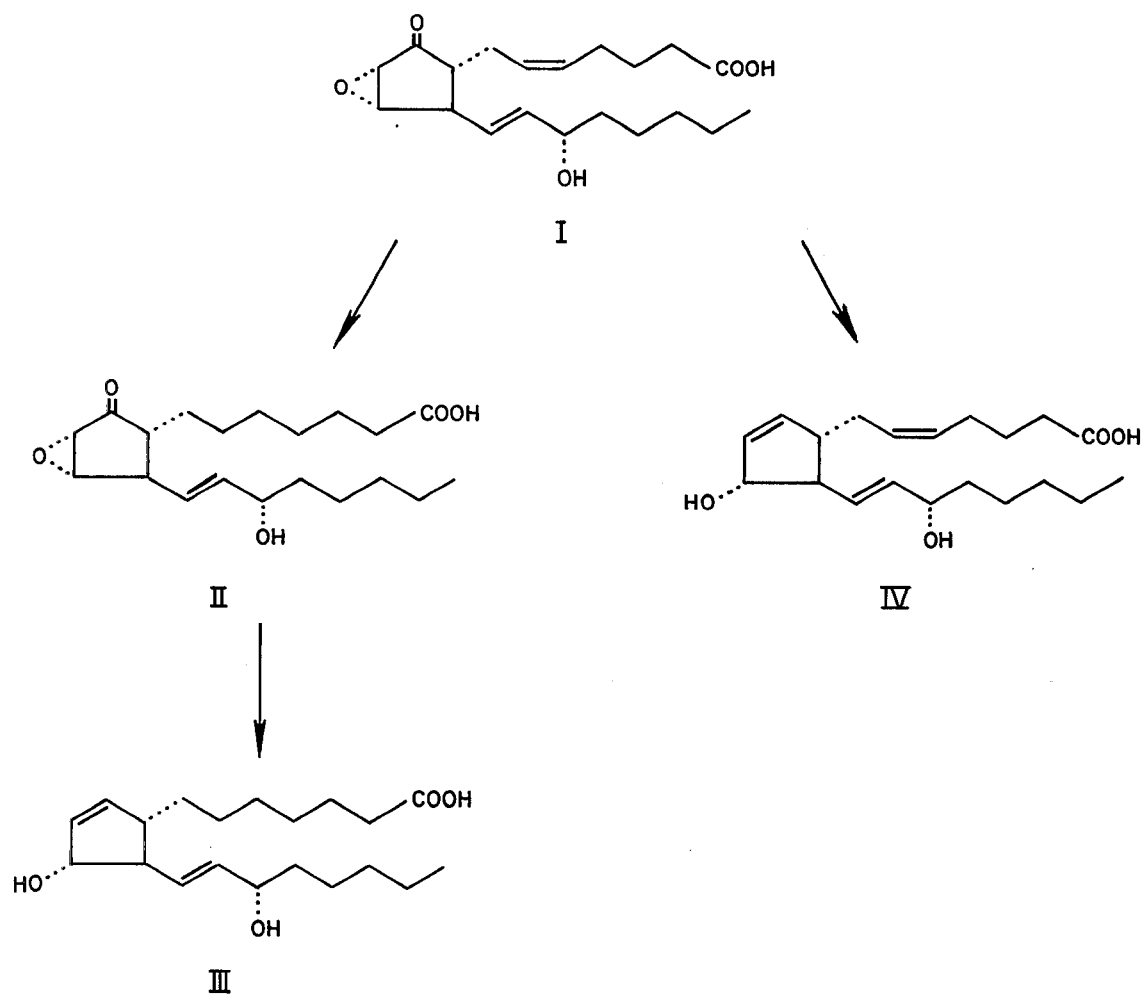

In describing the synthesis of the compositions of the invention, reference will be made to FIG. 1, wherein is illustrated the preparation of specific embodiments of the invention, and wherein the formulae representing the various aspects of the invention are assigned Roman numerals for purposes of identification. Additionally, in order to designate the stereochemistry of various substituents on the prostaglandin skeleton, different types of lines are utilized when representing the bonds of said substituents. Thus, with reference to the plane of the paper, when a dashed line (----) is used, the substituent will be understood to be in the α (down) configuration. For purposes of convenience, the formulae in FIG. 1 are all free carboxylic acids; however, it will be obvious to those skilled in the art that these free acids may readily be esterified as for example with diazomethane, or with an alkanol and the proper catalyst. These esters are considered to be full equivalents to the free acids for the purposes of the invention. Finally, the use of specific embodiments in FIG. 1 to illustrate the invention is merely descriptive and is not intended to delimit the scope of the invention.

The starting material for the synthesis of the compounds of the invention is 10,11α-epoxy-PGA$_2$ (I) which may be prepared synthetically as described, for example, in J. Org. Chem., 38, 3187 (1973). Referring now to FIG. 1, the 5,6-double bond of 10,11α-epoxy-PGA$_2$ (I) may first be selectively reduced by reaction with tris(triphenyl)rhodium (I) chloride. This reaction is best carried out by prehydrogenating a solution of tris(triphenyl)rhodium (I) chloride in 1:1 benzene:ethanol, adding I in 1:1 benzene:ethanol solution and further hydrogenating at atmospheric pressure until 1 equivalent of hydrogen is absorbed. The resulting mono-ene II is next treated with hydrazine to produce the allylic alcohol III (see for example, J. Org. Chem., 26, 3615 [1961]). Alternatively, the diene I, may be reacted with hydrazine producing the allylic alcohol IV.

Various compounds of the invention bear carboxyl groups and can be readily converted to their respective alkali metal salts or a salt of a pharmacologically acceptable cation derived from ammonia of a basic amine. All such salts are full equivalents of the subject matter particularly claimed.

In using the compounds of the invention to produce bronchodilating effects in warm-blooded animals, they may be administered in a variety of dosage forms: oral, injectable, and aerosol inhalation. Aerosol inhalation is a preferred method because of its rapid onset of action, great potency, and specificity of action. The particular dosage to obtain the bronchodilating effect will vary with the particular compound employed, the particular animal involved, and the degree of bronchodilation desired. In the guinea pig, by aerosol inhalation, the dose to produce bronchodilation is from about 1.5 micrograms to about 100 micrograms, and preferably from about 1.5 to about 50 micrograms. The bronchodilation produced upon aerosol inhalation can be observed by the method of Rosenthale et al., J. Pharmacol. Exp. Ther., 178, 541 (1971). Using this procedure the following result was obtained.

| Compound | Dose (μg) | Percent Inhibition of the bronchoconstricting effects of a standard dose of acetylcholine |
|---|---|---|
| 7-(4α-hydroxy-5β-[(3S)-3-hydroxy-trans-1-octenyl]-2-cyclopenten-1α-yl)-cis-5-heptenoic acid | 15 | 44 |
| 4α-hydroxy-5β-[(3S)-3-hydroxy-trans-1-octenyl]-2-cyclopentene-1α-heptanoic acid | 1.5 | 60 |

In the use of the compounds of the invention to produce hypotensive effects in warm-blooded animals, administration by the injectable route is preferred, preferably the intravenous route.

Thus in the anesthetized dog by the intravenous route the dose to produce hypotension is from about 1 μg/kg. to about 200 μg/kg. and preferably from about 10 μg/kg. to about 100 μg/kg. Using this procedure the following results were obtained.

| Compound | Dose (μg/kg) | Δb.p. (mm. Hg) |
|---|---|---|
| 4α-hydroxy-5β-[(3S)-3-hydroxy-trans-1-octenyl]-2-cyclopentene-1α-heptanoic acid | 100 | −34 |

In the rat by the subcutaneous route the dose to inhibit gastric secretion is from about 0.1 mg/kg. to about 25 mg/kg. and preferably from about 1.0 mg/kg. to about 10 mg/kg. The reduction in gastric secretion can be observed by a modification of the method of Shay et al., Gastroenterology, 26, 906 (1954). Using this procedure the following results were obtained.

| Compound | Dose (mg/kg.) | Results |
|---|---|---|
| 7-(4α-hydroxy-5β-[(3S)-3-hydroxy-trans-1-octenyl]-2-cyclopenten-1α-yl)-cis-5-heptenoic acid | 4 | Statistically significant decrease in hydrogen ion concentration and in total hydrogen ion secreted |
| 4α-hydroxy-5β-[(3S)-3-hydroxy-trans-1-octenyl]-2-cyclopentene-1α-heptanoic acid | 4 | Statistically significant decrease in hydrogen ion concentration and in total hydrogen ion secreted |

Platelet aggregation is the initial step in thrombus formation and it is considered that compounds which prevent aggregation or reduce platelet adhesiveness may inhibit the initiation of the arteriosclerotic process. The effect of drugs on aggregation is measured in platelet rich plasma (PRP) containing adenosine diphosphate (ADP) which markedly increases aggregation in vitro and may be a physiological agent for doing so in vivo.

To demonstrate utility as blood platelet anti-aggregation agents for following procedure is followed (modification of the procedure of Born, G. V. R., and Cross, M. J., J. Physiol. 168, 178–195, 1963).

Human blood is collected from fasted normal blood donors in siliconized 50 ml. Vacutainers that contain 3.8% sodium citrate. Centrifugation at 500 G. for 3 minutes at 5° C. separates the red blood cells from the PRP. The supernatant PRP is pipetted off and the remainder is centrifuged at 1000 G. for 10 minutes at 25° C. to obtain platelet poor plasma for standardization of the automated Payton aggregometer. In the running of the platelet aggregation test a cell containing 1.0 ml. of PRP is stirred at 1,100 rpm and the test compound is added in 0.2 ml. of buffered saline to give an initial concentration of $5 \times 10^{-3}$M, or $5 \times 10^{-4}$M. After 3 minutes, a concentration of ADP predetermined to yield marked platelet aggregation (2 to 4 $\mu$M) is added in 0.1 ml. of buffered saline. The curve of light transmission at 610 m$\mu$ is followed for 6 minutes. Compounds found to be active at the initial concentration are run at lower concentrations. The results are expressed as the concentration which gives 50% inhibition of the ADP induced aggregation.

Using this procedure the following results are obtained for the compounds of the invention.

| Compound | Inhibition of ADP Induced platelet aggregation (at concentration | Concentration which inhibits 50% of platelet aggregation |
|---|---|---|
| 7-(4$\alpha$-hydroxy-5$\beta$-[(3S)-3-hydroxy-trans-1-octenyl]-2-cyclopenten-1$\alpha$-yl)-cis-5-heptenoic acid | 50% (2.6 × 10$^{-6}$M) | 2.6 × 10$^{-6}$M |
| 4$\alpha$-hydroxy-5$\beta$-[(3S)-3-hydroxy-trans-1-octenyl]-2-cyclopentene-1$\alpha$-heptanoic acid | 63% (1.5 × 10$^{-6}$M) | 1.2 × 10$^{-6}$M |

The following examples further illustrate the best mode contemplated by the inventor for the practice of the invention.

EXAMPLE 1

2$\beta$-[(3S)-3-Hydroxy-Trans-1-Octenyl]-4-Oxo-6-Oxabicyclo[3.1.0]hex-3$\alpha$-Ylheptanoic Acid (II)

A solution of 2.58 g. of 7-(2$\beta$-[(3S)-3-hydroxy-trans-1-octenyl]-4-oxo-6-oxabicyclo[3.1.0]hex-3$\alpha$-yl)-cis-5-heptenoic acid in 135 ml. of 1:1 benzene:ethanol was added to a prehydrogenated solution of 1.27 g. of tris(-triphenyl)rhodium (I) chloride in 135 ml. of 1:1 benzene:ethanol and the mixture hydrogenated at atmospheric pressure and 25° until 1 equivalent of hydrogen was absorbed. The solvent was evaporated and the residue chromatographed on silica with 30% ethyl acetate-hexane to obtain 1.297 g. of 2$\beta$-[(3S)-3-hydroxy-trans-1-octenyl]-4-oxo-6-oxabicyclo[3.1.0]hex-3$\alpha$-ylheptanoic acid as an oil, $\lambda_{max}^{film}$ 3.0 (shoulder), 3.45, 5.75, 8.5, 10.25, 11.9 $\mu$ NMR: $\delta$ 5.65 (m, 2, 13 and 14-H), 4.15 (m, 1, 15-H), 3.78 (m, 1, 10-H), 3.45 (m, 1, 9-H) ppm. Mass spectrum: M$^+$ at m/e 352.

EXAMPLE 2

4$\alpha$-Hydroxy-5$\beta$-[(3S)-3-Hydroxy-Trans-1-Octenyl]-2-Cyclopentene-1$\alpha$-Heptanoic Acid (III)

Treat a solution of 1.175 g. of 2$\beta$-[(3S)-3-hydroxy-trans-1-octenyl]-4-oxo-6-oxabicyclo[3.1.0]hex-3$\alpha$-ylheptanoic acid in 45 ml. of methanol with 0.44 ml. of 95% hydrazine and 0.055 ml. of acetic acid and stir the mixture at 25° for 0.5 hours under nitrogen. Dilute the reaction mixture with water, acidify with acetic acid and extract with ether. After washing and drying, evaporate the ether extract and chromatograph the residue on silica with 50% ethyl acetate in hexane to obtain 0.26 g. of 4$\alpha$-hydroxy-5$\beta$-[(3S)-3-hydroxy-trans-1-octenyl]-2-cyclopentene-1$\alpha$-heptanoic acid as an oil, $\lambda_{max}^{film}$ 3.0, 3.4, 5.8, 6.8, 10.25 $\mu$. NMR: $\delta$ 5.5-6.0 (m, 4, olefinic H), 4.55 (m, 1, 11-H), 4.10 (m, 1, 15-H) ppm. Mass spectrum: M$^+$ —H$_2$O at m/e 320.2340 (theory 320.2350).

EXAMPLE 3

7-(4$\alpha$-Hydroxy-5$\beta$-[(3S)-3-Hydroxy-Trans-1-Octenyl]-2-Cyclopenten-1$\alpha$-Yl)-Cis-5-Heptenoic Acid (IV)

A solution of 0.644 g. of 7-(2$\beta$-[(3S)-3-hydroxy-trans-1-octenyl]-4-oxo-6-oxabicyclo[3.1.0]hex-3$\alpha$-yl)-cis-5-heptenoic acid in 25 ml. of methanol was treated with 0.25 ml. of hydrazine and 0.03 ml. of acetic acid and the mixture stirred at 25° for ½ hour under nitrogen. The mixture was diluted with water, acidified with acetic acid and extracted with ether. After washing and drying, the extract was evaporated and the residue chromatographed on silica with 50% ethyl acetate-hexane to obtain 0.198 g. of 7-(4$\alpha$-hydroxy-5$\beta$-[(3S)-3-hydroxy-trans-1-octenyl]-2-cyclopenten-1$\alpha$-yl)-cis-5-heptenoic acid as an oil, $\lambda_{max}^{film}$ 3.05, 3.45, 5.85, 8.1, 10.3 $\mu$. NMR: $\delta$ 5.2-6.0 (m, 6, olefinic H), 4.6 (m, 1, 11-H), 4.1 (m, 1, 15-H) ppm. Mass spectrum: MH$^+$—H$_2$O at m/e 319.

The subject matter which the applicant regards as his invention is particularly pointed out and distinctly claimed as follows:

1. A chemical compound of the structure:

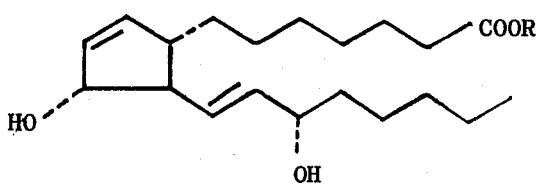

wherein R is hydrogen or alkyl of from 1 to 6 carbon atoms.

2. The compound of claim 1 wherein R is hydrogen.

* * * * *